United States Patent
Hansen, Jr. et al.

(10) Patent No.: US 6,465,518 B2
(45) Date of Patent: Oct. 15, 2002

(54) HALOGENATED 2-AMINO-4, 5 HEPTENOIC ACID DERIVATIVES USEFUL AS NITRIC OXIDE SYNTHASE INHIBITORS

(75) Inventors: Donald W. Hansen, Jr., Skokie, IL (US); Ronald Keith Webber, St. Charles, MO (US); Alok K. Awasthi, Skokie, IL (US); Pamela T. Manning, Labadie, MO (US)

(73) Assignee: Pharmacia Corporation, Skokie, IL (US)

( * ) Notice: Subject to any disclaimer, the term of this patent is extended or adjusted under 35 U.S.C. 154(b) by 0 days.

(21) Appl. No.: 09/834,361

(22) Filed: Apr. 13, 2001

(65) Prior Publication Data

US 2002/0037927 A1 Mar. 28, 2002

Related U.S. Application Data

(60) Provisional application No. 60/196,694, filed on Apr. 13, 2000.

(51) Int. Cl.$^7$ ............................................. A01N 37/12
(52) U.S. Cl. ....................................... 514/565; 562/560
(58) Field of Search ................... 562/561, 540, 562/512, 553, 598, 602, 605, 560; 574/565

(56) References Cited

U.S. PATENT DOCUMENTS

| | | | |
|---|---|---|---|
| 5,132,453 A | 7/1992 | Griffith | 562/560 |
| 5,684,008 A | 11/1997 | Hallinan et al. | 514/256 |
| 5,830,917 A | 11/1998 | Moore et al. | 514/634 |
| 5,854,251 A | 12/1998 | Hallinan et al. | 514/256 |
| 5,863,931 A | 1/1999 | Beams et al. | 514/357 |
| 5,919,787 A | 7/1999 | Hallinan et al. | 514/256 |
| 5,945,408 A | 8/1999 | Webber et al. | 514/63 |
| 5,981,511 A | 11/1999 | Gapud et al. | 514/63 |
| 5,994,391 A | 11/1999 | Lee et al. | 514/431 |
| 6,169,089 B1 | 1/2001 | Hallinan et al. | 514/256 |

FOREIGN PATENT DOCUMENTS

| | | | | |
|---|---|---|---|---|
| EP | 04 46699 | | 5/2000 | C07K/5/06 |
| EP | 05 21471 | | 10/2000 | C07D/239/42 |
| WO | WO 93 13055 | | 7/1993 | C07C/257/14 |
| WO | WO 93 16055 | | 8/1993 | C07D/281/10 |
| WO | WO 94 12165 | | 6/1994 | A61K/31/155 |
| WO | WO 94 14780 | | 7/1994 | C07D/239/48 |
| WO | WO 95 11014 | | 4/1995 | A61K/31/00 |
| WO | WO 95 11231 | | 4/1995 | C07D/207/22 |
| WO | WO 95/24382 | * | 9/1995 | C07C/257/14 |
| WO | WO 95 25717 | | 9/1995 | C07C/257/14 |
| WO | WO 96 15120 | | 5/1996 | C07D/257/06 |
| WO | WO 96 33175 | | 10/1996 | C07D/223/12 |
| WO | WO 96 35677 | | 11/1996 | C07D/223/12 |
| WO | WO 97 06802 | | 2/1997 | A61K/31/495 |
| WO | WO 99 29865 | | 6/1999 | C12N/15/28 |
| WO | WO 99 46240 | | 9/1999 | C07C/257/14 |

OTHER PUBLICATIONS

S. Moncada and E. Higgs, *Molecular Mechanisms and Therapeutic Strategies Related to Nitric Oxide* 1995, FASEB J., 9, 1319–1330.

S. Rozen, I. Shahak, and E. Bergmann, *Organic Fluorine Compounds Part XLIV. Preparation and Reactions of Epifluorohydrin* 1971, Synthesis 646–7.

E. Bergmann, S. Cohen, and I. Shahak, *Organic Fluorine Compounds. Part XX. Some Reactions of 1–Chloro–3–fluoropropan–2–ol and Epifluorohydrin* 1961, J Chem Soc 3448–52.

A. Jeanguenat and D. Seebach, *Stereoselective Chain Elongation at C–3 of Cysteine through 2,3–Dihydrothiazoles, Without Racemization. Preparation of 2–Amino–5–hydroxy–3–mercapto alkanoic Acid Derivatives.* 1991, J. Chem. Soc. Perkin Trans. 1, 2291–8.

G. Pattenden, S. Thom, and M. Jones, *Enantioselective Synthesis of 2–Alkyl Substituted Cysteines.* 1993, Tetrahedron, 49, 2131.

D. Bredt and S. Snyder, *Isolation of nitric oxide synthetase, a calmodulin–requiring enzyme.* 1990 Proc. Natl. Acad. Sci. U.S.A., 87, 682–685.

Moore et al, *2–Iminopiperidine and Other 2–Iminoazaheterocycles as Potent Inhibitors of Human Nitric Oxide Synthase Isoforms* 1996 J. Med. Chem., 39, 669–672.

T. Misko et al, *A Fluorometric Assay for the Measurement of Nitrite in Biological Samples* 1993, Analytical Biochemistry, 214, 11–16.

Y. Lee et al., *Conformationally–restricted Arginine Analogues as Alternative Substrates and Inhibitors of Nitric Oxide Synthases* 1999 Bioorg. Med. Chem. 7 1097–1104.

R. Young et al., *Inhibition of Inducible Nitric Oxide Synthase by Acetamidine Derivatives of Hetero–Substituted Lysine and Homolysine* 2000 Bioorg. Med. Chem. Lett. 10 597–600.

* cited by examiner

*Primary Examiner*—Paul J. Killos
(74) *Attorney, Agent, or Firm*—Philip B. Polster, II

(57) ABSTRACT

The present invention contains halogenated 2-amino-4,5 heptenoic acid derivatives useful as nitric oxide synthase inhibitors.

76 Claims, No Drawings

HALOGENATED 2-AMINO-4, 5 HEPTENOIC ACID DERIVATIVES USEFUL AS NITRIC OXIDE SYNTHASE INHIBITORS

This application claims the benefit of U.S. Provisional Application No. 60/196,694, filed Apr. 13, 2000.

FIELD OF THE INVENTION

The present invention relates to halogenated amidino compounds and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:
(i) a constitutive, $Ca^{++}$/calmodulin dependent enzyme, located in the endothelium, that releases NO in response to receptor or physical stimulation.
(ii) a constitutive, $Ca^{++}$/calmodulin dependent enzyme, located in the brain, that releases NO in response to receptor or physical stimulation.
(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds that inhibit nitric oxide synthesis and preferentially inhibit the inducible isoform of nitric oxide synthase:
International Publication No. WO 96/35677
International Publication No. WO 96/33175
International Publication No. WO 96/15120
International Publication No. WO 95/11014
International Publication No. WO 95/11231
International Publication No. WO 95/25717
International Publication No. WO 95/24382
International Publication No. WO 94/12165
International Publication No. WO 94/14780
International Publication No. WO 93/13055
European Patent Application No. EP0446699A1
U.S. Pat. No. 5,132,453
U.S. Pat. No. 5,684,008
U.S. Pat. No. 5,830,917
U.S. Pat. No. 5,854,251
U.S. Pat. No. 5,863,931
U.S. Pat. No. 5,919,787
U.S. Pat. No. 5,945,408
U.S. Pat. No. 5,981,511
International Publication No. WO 95/25717 discloses certain amidino derivatives as being useful in inhibiting inducible nitric oxide synthase.
International Publication No. WO 99/62875 discloses further amidino compounds as being useful in inhibiting inducible nitric oxide synthase.
In particular WO 99/46240 discloses compounds of formula

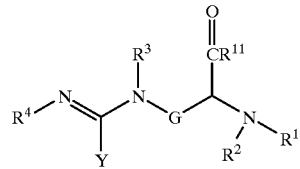

or a pharmaceutically acceptable salt thereof, wherein:
$R^1$ is selected from the group consisting of hydrogen, $C_1$–$C_{10}$ alkyl, $C_2$–$C_{10}$ alkenyl, and $C_2$-$C_{10}$ alkynyl;
$R^2$ is selected from the group consisting of hydrogen, $C_1$–$C_{10}$ alkyl, $C_2$–$C_{10}$ alkenyl, $C_2$–$C_{10}$ alkynyl, and either R or S alpha-amino acid;
$R^3$ and $R^4$ are independently selected from the group consisting of hydrogen, $C_1$–$C_{10}$ alkyl, $C_2$–$C_{10}$ alkenyl, $C_2$–$C_{10}$ alkynyl, and $NO_2$;
wherein $R^1$, $R^2$, $R^3$ and $R^4$ can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, and guanidino;
$R^{11}$ is selected from the group consisting of hydroxyl and R or S alpha-amino acid;
G is selected from the group consisting of $C_1$–$C_{10}$ alkylene, $C_2$–$C_{10}$ alkenylene, and $C_2$–$C_{10}$ alkynyl, each of which is optionally substituted with one or more selected from the group consisting of halogen, hydroxy, trifluoromethyl, nitro, cyano, amino, $C_1$–$C_{10}$ alkyl, $=CH_2$, $C_2$–$C_{10}$ alkenyl, $C_2$–$C_{10}$ alkynyl, and $C_1$–$C_{10}$ alkoxy, each of which can be can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

G is selected from the formula $(CH_2)_p$—$(CX^1X^2)_r$—$(CH_2)_s$—Q—$(CH_2)_t$—$(CX^3X^4)_u$—$(CH_2)_v$ where p, r, s, t, u, v are independently 0 to 3 and Q is oxygen, $C=O$, $S(O)_a$ wherein a is 0 to 2, with the proviso that when a is 1 or 2, G must contain halogen, or $NR^{12}$ wherein $R^{12}$ is hydrogen or $C_1$–$C_{10}$ alkyl which may be optionally substituted with one or more selected from the group consisting of $C_1$–$C_{10}$ alkyl, $C_1$–$C_{10}$ alkoxy, hydroxy, trifluoromethyl, nitro, cyano, amino, and halogen;

G is selected from the formula —$(CH_2)_w$—$(CX^5X^6)_y$—$(CH_2)_z$—A—$(CH_2)_k$—$(CX^7X^8)_j$—$(CH_2)_h$ wherein w, y, z, k, j, h are independently 0 to 3 and A is a 3 to 6 membered carbocyclic radical or heterocyclic radical which may be optionally substituted with one or more selected from the group consisting of halogen, $C_1$–$C_{10}$ alkyl, $C_1$–$C_{10}$ alkoxy, hydroxy, trifluoromethyl, nitro, cyano, and amino, each of which may be optionally substituted with halogen or $C_1$–$C_{10}$ alkyl, with the proviso that when G is selected from the formula —$(CH_2)_w$—$(CX^5X^6)_y$—$(CH_2)_z$—A—$(CH_2)_k$—$(CX^7X^8)_j$—$(CH_2)_h$, Y must contain halogen;

$X^1$, $X^2$, $X^3$, $X^4$, $X^5$, $X^6$, $X^7$, $X^8$ are independently not present, hydrogen, halogen, $C_1$–$C_{10}$ alkyl, $=CH_2$, $C_2$–$C_{10}$ alkenyl, or $C_2$–$C_{10}$ alkynyl, wherein $C_1$–$C_{10}$ alkyl, $=CH_2$, $C_2$–$C_{10}$ alkenyl, and $C_2$–$C_{10}$ alkynyl can be optionally substituted with one or more from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

Y is selected from the group consisting of heterocycle, $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl, each of which is optionally substituted with one or more selected from the group consisting of halogen, hydroxy, trifluoromethyl, nitro, cyano, amino, $C_1$–$C_{10}$ alky, $C_2$–$C_{10}$ alkenyl, $C_2$–$C_{10}$ alkynyl, and $C_1$–$C_{10}$ alkoxy;

Y can be $NR^9R^{10}$ wherein $R^9$ and $R^{10}$ are independently selected from the group consisting of hydrogen, $C_1$–$C_{10}$ alkyl, $C_3$–$C_{10}$ cycloalkyl, $C_2$–$C_{10}$ alkenyl, $C_2$–$C_{10}$ alkynyl, nitro, amino, aryl, and $C_1$–$C_{10}$ alkaryl;

with the proviso that at least one of G or Y contains a halogen.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors.

SUMMARY OF THE INVENTION

Compounds have now been found which have the advantage of being very efficacious as iNOS inhibitors in the human cartilage explant assay, a model for osteoarthritis.

The present invention demonstrates that a halogenated carbon-carbon double bond can be used as a rigidifying element, and the resulting compounds have unexpected potency and selectivity for inhibition of inducible NOS.

Compounds of the present invention are unexpectedly potent and highly selective inhibitors of inducible nitric oxide synthase, and exhibit a relatively long half life in vivo. The compounds of the present invention may therefore optionally be administered efficaciously in divided doses, such as, for example, every other day or twice per week.

In a broad aspect, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

In one embodiment of the present invention, the compounds are represented by Formulas I, II and III:

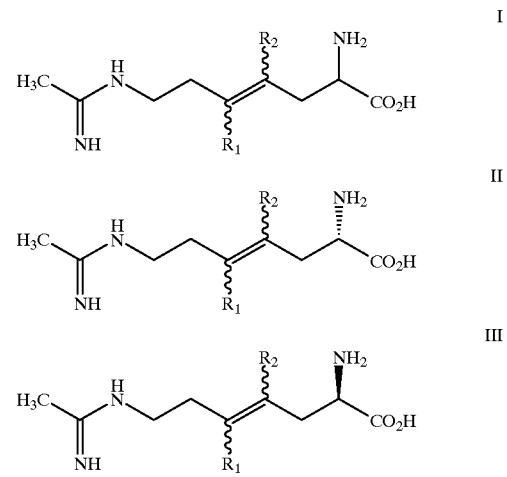

or a pharmaceutically acceptable salt thereof, wherein:

$R_1$ and $R_2$ are selected from the group consisting of H, alkyl, alkenyl, alkynyl, and halo wherein all but hydrogen and halo may be substituted by one or more hydroxy, alkyl, alkenyl, alkynyl, alkoxy, and halo;

with the proviso that at least one of $R_1$ or $R_2$ must contain a halogen.

DETAILED DESCRIPTION OF THE INVENTION

The present invention provides compounds having a halogenated carbon-carbon double bond, and these compounds have unexpected greater potency and selectivity for inhibition of inducible NOS.

Compounds of the present invention are unexpectedly potent and highly selective inhibitors of inducible nitric oxide synthase, and exhibit a relatively long half life in vivo as compared with known nitric oxide synthase inhibitors.

Compounds of Formulas I, II, III, IV, V and VI will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID or opioid analgesic would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, bums, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temporalmandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LYA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofuir, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku OF-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofirin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23–112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid). A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, norbinaltorphimine, naltrindole, DPDPE, [D-la$^2$, glu$^4$] deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

The term "alkyl", alone or in combination, means an acyclic alkyl radical, linear or branched, preferably containing from 1 to about 10 carbon atoms, more preferably containing from 1 to about 6 carbon atoms, and still more preferably about 1 to 3 carbon atoms. "Alkyl" also encompasses cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, isoamyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, 2-chloropropylenyl, buten-1-yl, isobutenyl, penten1-yl, 2-methylbuten-1-yl, 3-methylbuten-1-yl, hexen-1-yl, 3-hydrozyhexen-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "alkoxy" embrace linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of "lower alkylthio" is methylthio ($CH_3$—S—).

The term "alkylthioalkyl" embraces alkylthio radicals, attached to an alkyl group. Examples of such radicals include methylthiomethyl.

The term "halo" means halogens such as fluorine, chlorine, bromine or iodine atoms.

The term "heterocyclyl" means a saturated or unsaturated mono-or multi-ring carbocycle wherein one or more carbon atoms is replaced by N, S, P, or O. This includes, for example, the following structures:

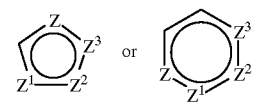

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C. The term "heterocyclyl" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocyclyl" also includes partially unsaturated ring structures such as dihydrofuranyl, pyrazolinyl, imidazolinyl, pyrrolinyl, chromanyl, dihydrothiophenyl, and others.

The term "heteroaryl" means a fully unsaturated heterocycle.

In either "heterocycle" or "heteroaryl," the point of attachment to the molecule of interest can be at the heteroatom or elsewhere within the ring.

The term "cycloalkyl" means a mono-or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" additionally encompasses spiro systems.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring carbocycle, including, but not limited to, substituted or unsubstituted phenyl, naphthyl, or anthracenyl.

The term "combination therapy" means the administration of two or more therapeutic agents to treat a therapeutic condition or disorder described in the present disclosure, for example atherosclerosis, pain, inflammation, migraine, neoplasia, angiogenisis-related condition or disorder, or other. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to include and qualify a combined amount of active ingredients in a combination therapy. This combined amount will achieve the goal of ameliorating the symptoms of, reducing or eliminating the targeted condition.

In its broadest aspect, compounds of the present invention are represented by Formula I, II, or III

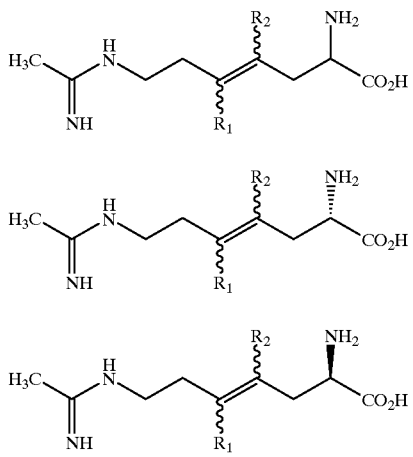

or a pharmaceutically acceptable salt thereof, wherein:
  $R_1$ is selected from the group consisting of hydrogen, alkyl, alkenyl, alkynyl, and halo wherein all but hydrogen and halo and halo may be substituted by one or more hydroxy, alkyl, alkenyl, alkynyl, alkoxy, and halo;
  $R_2$ is selected from the group consisting of hydrogen, alkyl, alkenyl, alkynyl, and halo wherein all but hydrogen and halo and halo may be substituted by one or more hydroxy, alkyl, alkenyl, alkynyl, alkoxy, and halo;
with the proviso that at least one of $R_1$ or $R_2$ must contain a halogen.

In another embodiment, compounds of the present invention are of Formula I, II or III wherein:
  $R_1$ is halo; and
  $R_2$ is selected from the group consisting of hydrogen, alkyl, alkenyl, alkynyl, and halo wherein all but hydrogen and halo may be substituted by one or more hydroxy, alkyl, alkenyl, alkynyl, alkoxy, and halo.

Another embodiment of the invention includes compounds of the present invention of Formula I, II or III wherein:
  $R_1$ is selected from the group consisting of hydrogen, alkyl, alkenyl, alkynyl, and halo wherein all but hydrogen and halo may be substituted by one or more hydroxy, alkyl, alkenyl, alkynyl, alkoxy, and halo; and
  $R_2$ is halo.

In an additional embodiment, the invention includes compounds of the present invention of Formula I, II or III wherein:
  $R_1$ is halo or hydrogen;
  $R_2$ is halo or hydrogen;
with the proviso that at least one of $R_1$ or $R_2$ is halo.

In other embodiments, the invention includes compounds of the present invention of Formula I, II or III wherein:
  $R_1$ is halo; $R_2$ is selected from the group consisting of hydrogen, $C_1$–$C_3$ alkyl, and halo wherein all but hydrogen and halo may be substituted by one or more $C_1$–$C_3$ alkyl, $C_1$–$C_3$ alkoxy, and halo.
  $R_1$ is selected from the group consisting of hydrogen, $C_1$–$C_3$ alkyl, and halo wherein all but hydrogen and halo may be substituted by one or more $C_1$–$C_3$ alkyl, $C_1$–$C_3$ alkoxy, and halo; and
  $R_2$ is halo.
  $R_1$ is halo; and $R_2$ is halo.
  $R_1$ is fluorine; and $R_2$ is fluorine.

Methods of using the compounds of Formula I, II or III include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, lowering nitric oxide levels in a subject in need of such by administering a therapeutically effective amount of a compound of Formula I, lowering nitric oxide levels in a subject in need of such by administering a therapeutically effective amount of a pharmaceutical composition comprising a compound of Formula I.

The term "pharmaceutically-acceptable salts" embraces salts commonly used to form alkali metal salts and to form addition salts of free acids or free bases. The nature of the salt is not critical, provided that it is pharmaceutically acceptable. Pharmaceutically acceptable salts are particularly useful as products of the methods of the present invention because of their greater aqueous solubility relative to a corresponding parent or neutral compound. Such salts must have a pharmaceutically acceptable anion or cation. Suitable pharmaceutically-acceptable acid addition salts of compounds of the present invention may be prepared from inorganic acid or from an organic acid. Examples of such inorganic acids are hydrochloric, hydrobromic, hydroiodic, nitric, carbonic, sulfuric and phosphoric acid. Appropriate organic acids include from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. Suitable pharmaceutically acceptable acid addition salts of the compounds of the present invention when possible include those derived from inorganic acids, such as hydrochloric, hydrobromic, boric, fluoroboric, phosphoric, metaphosphoric, nitric, carbonic (including carbonate and hydrogen carbonate anions), sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable pharmaceutically acceptable base salts include ammonium salts, alkali metal salts such as sodium and potassium salts, and alkaline earth salts such as magnesium and calcium salts. All of these salts may be prepared by conventional means from the corresponding conjugate base or conjugate acid of the compounds of the present invention by reacting, respectively, the appropriate acid or base with the conjugate base or conjugate acid of the compound. Another pharmaceutically acceptable salt is a resin-bound salt.

While it may be possible for the compounds of the present invention to be administered as the raw chemical, it is preferable to present them as a pharmaceutical composition. According to a further aspect, the present invention provides a pharmaceutical composition comprising a compound of the present invention or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of The present invention or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 200 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 50 mg, usually around 1 mg to 20 mg.

The compounds of Formula I, II or III are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereon, E-and Z-geometric isomers and mixtures thereof, R- and and S-enantiomers, diastereomers, d-isomers, 1-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present. Some of the compounds described contain one or more geometric isomers and are meant to include E, Z and mixtures of Z and E isomers.

The following general synthetic sequences are useful in making the present invention.

SCHEME 1
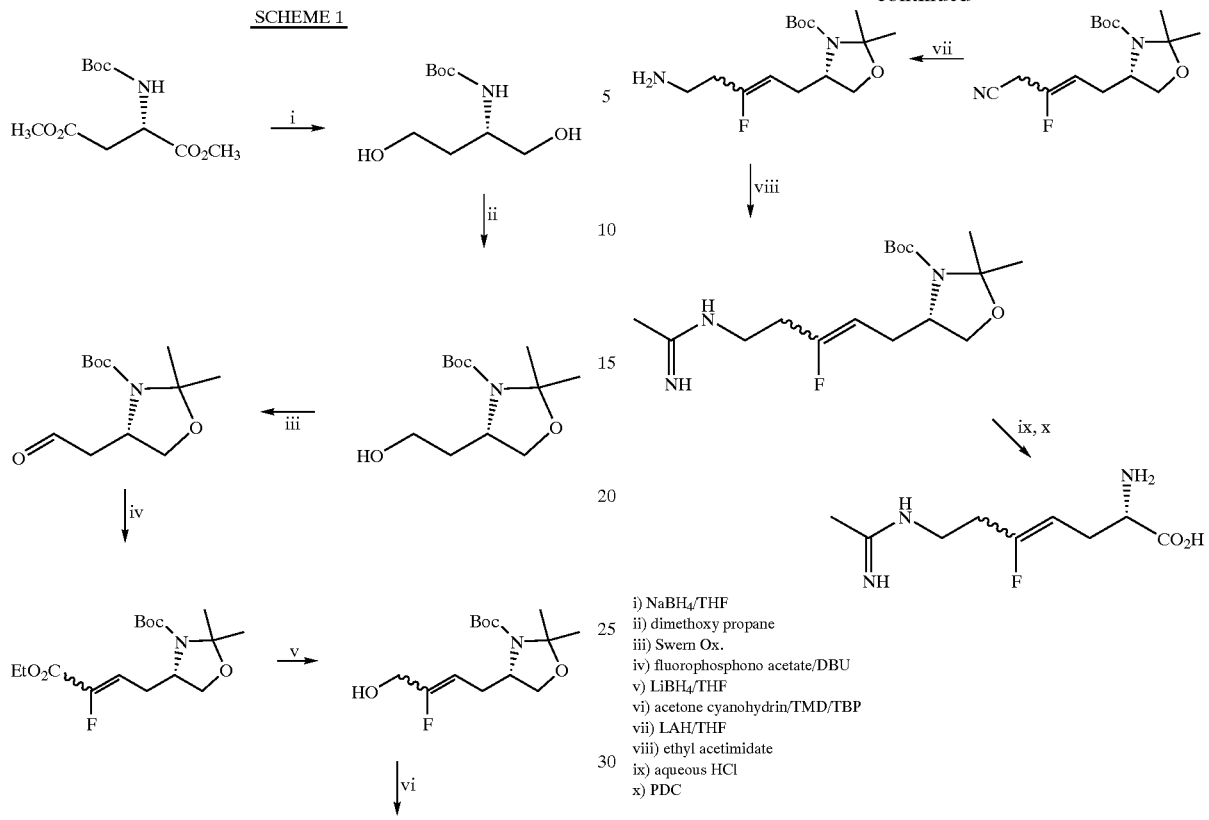
i) NaBH$_4$/THF
ii) dimethoxy propane
iii) Swern Ox.
iv) fluorophosphono acetate/DBU
v) LiBH$_4$/THF
vi) acetone cyanhydrin/TMD/TBP
vii) LAH/THF
viii) ethyl acetimidate
ix) aqueous HCl
x) PDC
SCHEME 2
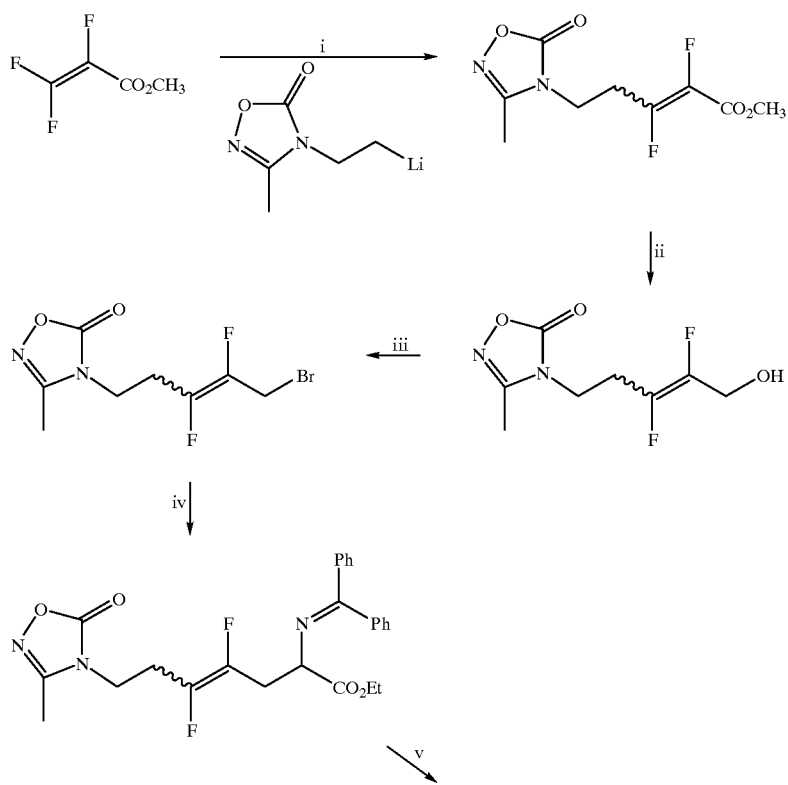

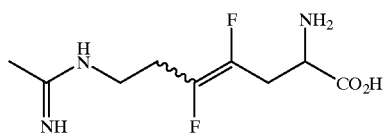

i) THF
ii) DIBAL/THF
iii) triphenyl phosphine/CBr$_4$
iv) benzophenone glycinate/KHMDS
v) 1) Zn/AcOH/H$_2$O 2) HCl

SCHEME 3

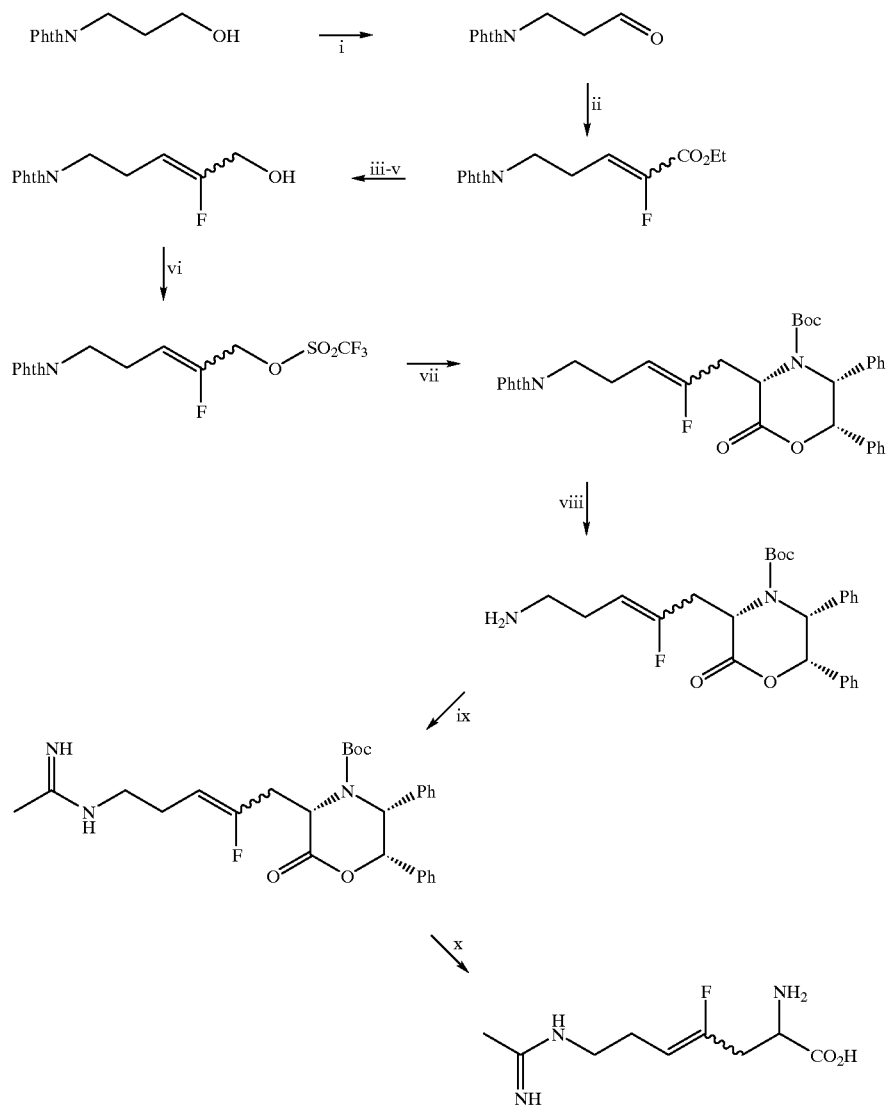

i) oxalyl chloride/DMSO
ii) fluorophosphonoacetate/DBU
iii) HCl/H$_2$O/acetone
iv) oxalyl chloride/CH$_2$Cl$_2$
v) NaBH$_4$/DMF
vi) Triflic anhydride/pyridine/CH$_2$Cl$_2$
vii) Williams' glycine/LiHMDS
viii) hydrazine/ethanol
ix) ethyl acetimidate
x) Na/NH$_3$(liq.)

SCHEME 4

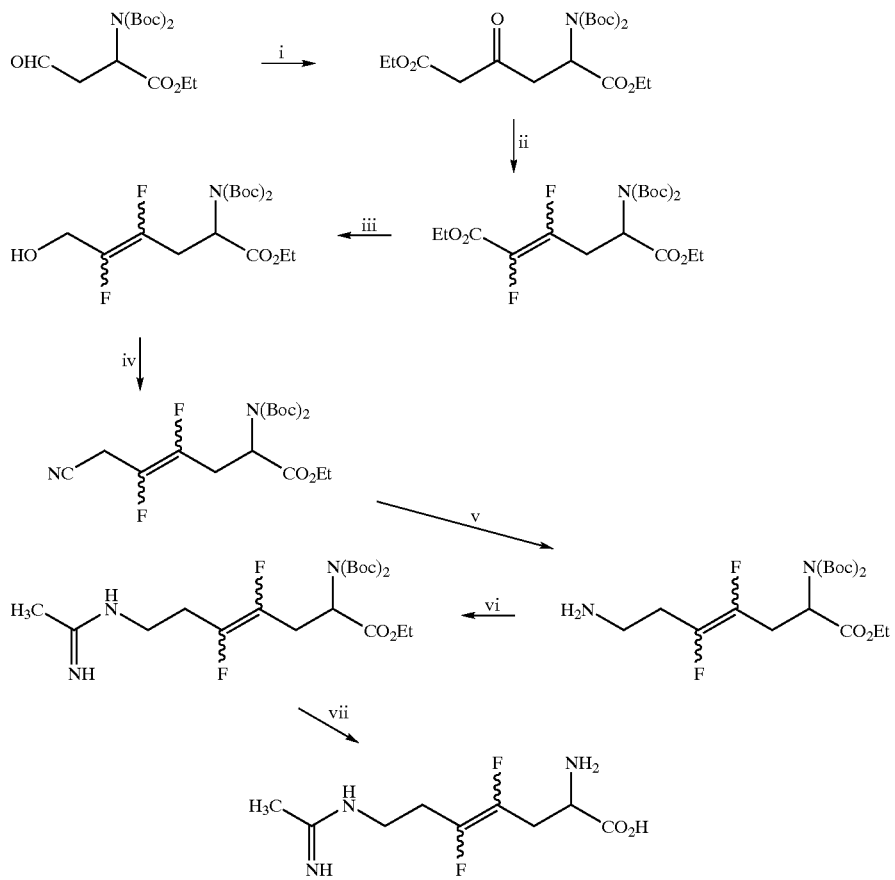

i) EtO₂C CHN₂/SnCl₄
ii) DAST
iii) DIBAL
iv) acetone cyanohydrin/TMD/TBP
v) DIBAL
vi) ethyl acetimidate
vii) aqueous HCl The following examples are provided to illustrate the present invention and are not intended to limit the scope thereof. Those skilled in the art will readily understand that known variations of the conditions and processes of the following preparative procedures can be used to prepare these compounds.

EXAMPLE 1

(2S,4E/Z)-2-Amino-5-Fluoro-6-(1-iminoethylamino)-hept-4-enoic acid

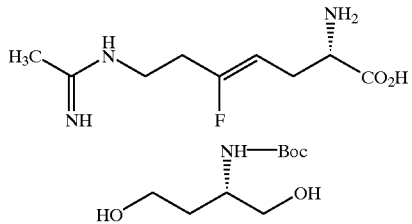

1a) 31.88 g (122 mmol) N^α-Boc-L-Asp(OMe)₂ was dissolved in the mixture of 100 mL THF and 10 mL methanol. The solution was cooled in an ice bath and it was treated with 9.45 g (250 mmol) NaBH₄ with stirring for 2 hours. The reaction was quenched with the slow addition of 10 mL sat. KHSO₄ and the solvent was evaporated in vacuo. The residue was dissolved in 200 mL sat. NaCl and extracted with 2×200 mL EtOAc, dried over MgSO₄ and the solvent was evaporated in vacuo to yield 12.1 g (59 mmol; 48%) clear oil. FAB MS: MH⁺=206.3 MNa⁺=228.3

1b) 14 g (68.3 mmol) dialcohol from step 1a was dissolved in 70 mL CH₂Cl₂ and reacted with 14.56 g (17.2 mL; 140 mmol) 2,2-dimethoxypropane for 18 hours in the presence of 1.9 g (10 mmol) p-toluene sulphonic acid. Then the solvent was evaporated in vacuo and the residue was dissolved in 300 mL EtOAc. It was washed with 2×200 mL saturated brine, dried over MgSO₄ and evaporated in vacuo to yield 14.9 g (61 mmol; 89%) as crude oil. FAB MS: MH⁺=246.2

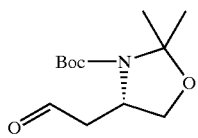

1c) 9.2 g (37.5 mmol) of the protected alcohol from step 1b, 25 mL DMSO and 18.9 g (187 mmol; 26.1 mL) triethylamine were mixed in 150 mL $CH_2Cl_2$ and cooled in an ice bath. 17.9 g (112 mmol) $SO_3$×pyridine complex was added to the mixture and it was stirred for 16 hours at room temperature. It was washed with 3×100 mL brine, dried over $MgSO_4$ and the solvent was evaporated in vacuo to yield 9.0 g (37 mmol; 99%) crude oil. FAB MS: $MH^+=244.2$

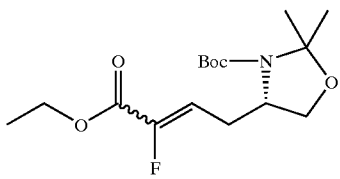

1d) In an ice bath 9.68 g (40 mmol) triethyl 2-fluoro-2-phosphono acetate in 100 mL $CH_2Cl_2$ was mixed with 6.8 g (45 mmol; 6.7 mL) DBU dissolved in 20 mL $CH_2Cl_2$. After stirring for 90 minutes, to the orange colored solution was added dropwise a solution of 9.0 g (37 mmol) of the aldehyde from step 1c in 50 mL $CH_2Cl_2$. The mixture was allowed to stir at room temperature for 16 hours. The solvent was evaporated in vacuo and the residue was dissolved in 300 mL EtOAc. It was washed with 200 mL 10% $KHSO_4$, 200 mL brine, dried over $MgSO_4$ and the solvent was evaporated in vacuo. Purification on a Biotage silica column eluting with EtOAc/hexane (1:5) yielded 8.1 g (24.5 mmol; 66%) clear oil. FAB MS: $MH^+=332.3$ and $MNH_4^+=349.3$

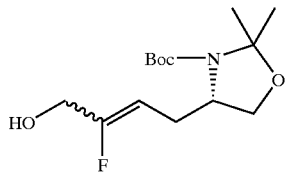

1e) 8.1 g (24.5 mmol) ethyl ester from step 1d was dissolved in 100 mL THF and it was reacted with 13 mL (26 mmol) $LiBH_4$ (2M solution in THF) in an ice bath and stirred for 16 hours at room temperature. The reaction was quenched with slow addition of 10% $KHSO_4$ in an ice bath. THF was evaporated in vacuo and the residue was dissolved in 250 mL EtOAc. It was washed with 100 mL 10% $KHSO_4$, 100 mL brine, dried over $MgSO_4$ and the solvent was evaporated in vacuo. Purification on a Biotage silica column eluting with EtOAc/hexane (1:4) yielded 5.34 g (18.4 mmol; 75%) clear oil. FAB MS: $MH^+=290.2$ and $MNH_4^+=307.3$

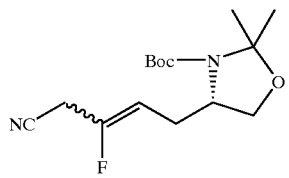

1f) 578 mg (2 mmol) alcohol from step 1e and 255 mg (0.275 mL; 3 mmol) acetone cyanohydrin were dissolved in 25 mL benzene. To this solution 516 mg (3 mmol) 1,1'-azobis(N,N-dimethylformamide) (TMD) and 606 mg (0.830 mL; 3 mmol) tri-n-butyl-phosphine (TBP) were added slowly and the mixture was stirred for 16 hours at room temperature. Benzene was evaporated in vacuo and the residue was dissolved in 200 mL EtOAc. It was washed with 100 mL brine, dried over $MgSO_4$ and the solvent was evaporated in vacuo. Purification on a Biotage silica column eluting with EtOAc/hexane (1:4) yielded 290 mg (0.97 mmol; 49%) clear oil. FAB MS: $MH^+=299.2$ and $MNH_4^+=316.3$

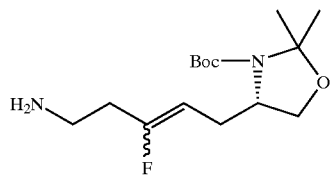

1g) The product of step 1f is allowed to react with lithium aluminum hydride in anhydrous THF to afford the title compound as a mixture of E and Z isomers. Chromatographic separation affords the Z isomer.

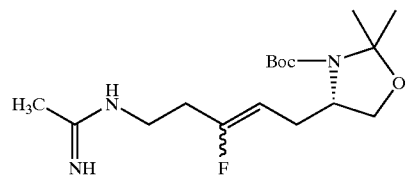

1h) The product of step 1g is allowed to react with ethyl acetimidate in ethanol to afford the title compound.

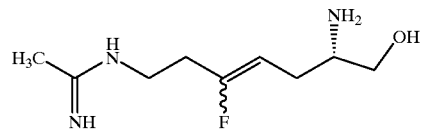

1i) The product of step 1h is allowed to stir in solution of aqueous HCl to afford the title compound.

1) The product of step 1i is allowed to react with PDC. Isolation and purification affords the title product.

EXAMPLE 2

(2S,4E)-2-Amino-5-Fluoro-6-(1-iminoethylamino)-hept-4-enoic acid

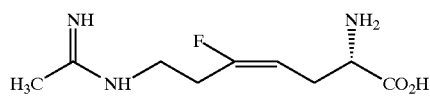

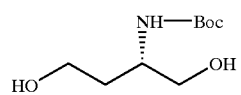

2a) 31.88 g (122 mmol) $N^\alpha$-Boc-L-Asp(OMe)$_2$ was dissolved in the mixture of 100 mL THF and 10 mL methanol. The solution was cooled in an ice bath and it was treated with 9.45 g (250 mmol) $NaBH_4$ with stirring for 2 hours. The reaction was quenched with the slow addition of 10 mL sat. $KHSO_4$ and the solvent was evaporated in vacuo. The residue was dissolved in 200 mL sat. NaCl and extracted with 2×200 mL EtOAc, dried over $MgSO_4$ and the solvent was evaporated in vacuo to yield 12.1 g (59 mmol; 48%) clear oil. FAB MS: $MH^+=206.3$ $MNa^+=228.3$

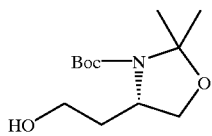

2b) 14 g (68.3 mmol) dialcohol from step 2a was dissolved in 70 mL CH$_2$Cl$_2$ and reacted with 14.56 g (17.2 mL; 140 mmol) 2,2-dimethoxypropane for 18 hours in the presence of 1.9 g (10 mmol) p-toluene sulphonic acid xH$_2$O. Then the solvent was evaporated in vacuo and the residue was dissolved in 300 mL EtOAc. It was washed with 2×200 mL saturated brine, dried over MgSO$_4$ and evaporated in vacuo to yield 14.9 g (61 mmol; 89%) as crude oil. FAB MS: MH$^+$=246.2

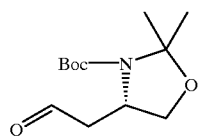

2c) 9.2 g (37.5 mmol) of the protected alcohol from step 2b, 25 mL DMSO and 18.9 g (187 mmol; 26.1 mL) triethylamine were mixed in 150 mL CH$_2$Cl$_2$ and cooled in an ice bath. 17.9 g (112 mmol) SO$_3$×pyridine complex was added to the mixture and it was stirred for 16 hours at room temperature. It was washed with 3×100 mL brine, dried over MgSO$_4$ and the solvent was evaporated in vacuo to yield 9.0 g(37 mmol; 99%) crude oil. FAB MS: MH$^+$=244.2

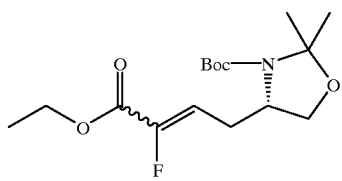

2d) In an ice bath 9.68 g (40 mmol) triethyl-2-fluoro-2-2-phosphono acetate in 100 mL CH$_2$Cl$_2$ was mixed with 6.8 g (45 mmol; 6.7 mL) DBU dissolved in 20 mL CH$_2$Cl$_2$. After stirring for 90 minutes, to the orange colored solution was added dropwise a solution of 9.0 g (37 mmol) of the aldehyde from step 2c in 50 mL CH$_2$Cl$_2$. The mixture was allowed to stir at room temperature for 16 hours. The solvent was evaporated in vacuo and the residue was dissolved in 300 mL EtOAc. It was washed with 200 mL 10% KHSO$_4$, 200 mL brine, dried over MgSO$_4$ and the solvent was evaporated in vacuo. Purification on a Biotage silica column eluting with EtOAc/hexane (1:5) yielded 8.1 g (24.5 mmol; 66%) clear oil. FAB MS: MH$^+$=332.3 and MNH$_4^+$=349.3

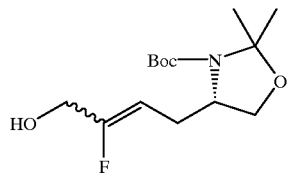

2e) 8.1 g (24.5 mmol) ethyl ester from step 2d was dissolved in 100 mL THF and it was reacted with 13 mL (26 mmol) LiBH$_4$ (2M solution in THF) in an ice bath and stirred for 16 hours at room temperature. The reaction was quenched with slow addition of 10% KHSO$_4$ in ice bath. THF was evaporated in vacuo and the residue was dissolved in 250 mL EtOAc. It was washed with 100 mL 10% KHSO$_4$, 100 mL brine, dried over MgSO$_4$ and the solvent was evaporated in vacuo. Purification on a Biotage silica column eluting with EtOAc/hexane (1:4) yielded 5.34 g (18.4 mmol; 75%) clear oil. FAB MS: MH$^+$=290.2 and MNH$_4^+$=307.3

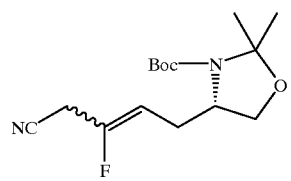

2f) 578 mg (2 mmol) alcohol from step 2e and 255 mg (0.275 mL; 3 mmol) acetone cyanohydrin were dissolved in 25 mL benzene. To this solution 516 mg (3 mmol) 1,1'-azobis(N,N-dimethylformamide) (TMD) and 606 mg (0.830 mL; 3 mmol) tri-n-butyl-phosphine (TBP) were added slowly and the mixture was stirred for 16 hours at room temperature. Benzene was evaporated in vacuo and the residue was dissolved in 200 mL EtOAc. It was washed with 100 mL brine, dried over MgSO$_4$ and the solvent was evaporated in vacuo. Purification on a Biotage silica column eluting with EtOAc/hexane (1:4) yielded 290 mg (0.97 mmol; 49%) clear oil. FAB MS: MH$^+$=299.2 and MNH$_4^+$=316.3

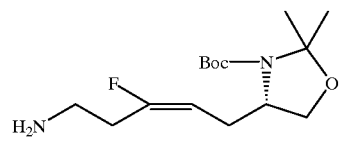

2g) The product of step 2f is allowed to react with lithium aluminum hydride in anhydrous THF to afford the title compound as a mixture of E and Z isomers. Chromatographic separation affords the E isomer.

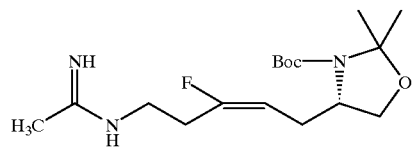

2h) The product of step 2g is allowed to react with ethyl acetimidate in ethanol to afford the title compound.

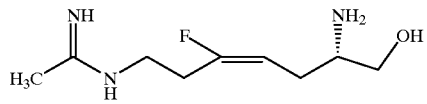

2i) The product of step 2h is allowed to stir in solution of aqueous HCl to afford the title compound.

2) The product of step 2i is allowed to react with PDC. Isolation and purification affords the title product.

EXAMPLE 3

(2R/S, 4E/Z)-2-Amino-4,5-difluoro-6-(1-iminoethylamino)-hept-4-enoic acid

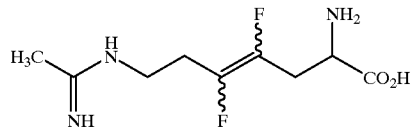

3a) To a solution of 3-methyl, 1,2,4-oxadiazolinone (prepared by the procedure of Tet. Let. 36(25), 4471–4474 (1995)) in acetone is added allyl bromide and potassium carbonate. This is stirred until complete by TLC. Isolation of the product by chromatography affords 3-methyl, 4-allyl, 1,2,4-oxadiazolinone.

3b) A solution of 3-methyl, 4-allyl, 1,2,4-oxadiazolinone is allowed to react with ozone, followed by workup conditions containing NaBH4. Isolation of the product afforded 3-methyl, 4-(2-hydroxyethyl), 1,2,4-oxadiazolinone.

3c) To a solution of 3-methyl, 4-(2-hydroxyethyl), 1,2,4-oxadiazolinone in methylene chloride is added triphenylphosphine and carbon tetrabromide. This is allowed to stir until complete by TLC. Isolation of the product affords 3-methyl, 4-(2-bromoethyl), 1,2,4-oxadiazolinone.

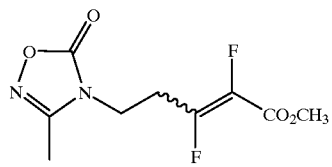

3d) To a solution of 3-methyl, 4-(2-bromoethyl), 1,2,4-oxadiazolinone in anhydrous THF at −78° C. is added sec-butyl lithium. To this stirred solution is then added methyl trifluoroacrylate. Isolation affords the title compound.

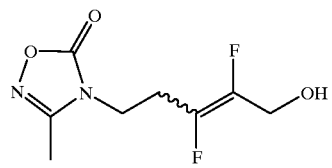

3e) To a solution of the product of example 3d in anhydrous THF is added DIBAL. Isolation affords the title product.

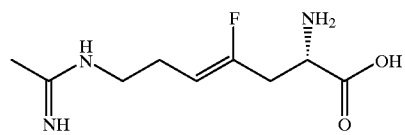

3f) The product of example 3e is subjected to the conditions of example 3c. Isolation affords the title product.

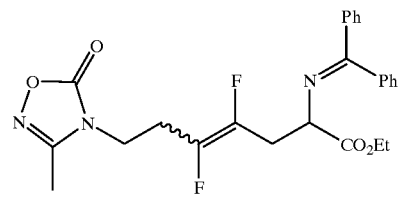

3g) To a solution of benzophenone imine of glycine ethyl ester in anhydrous THF is added lithium bistrimethylsilylamide at −78° C. To this mixture is slowly added the product of example 3f. The product is isolated by chromatography to afford the title compound.

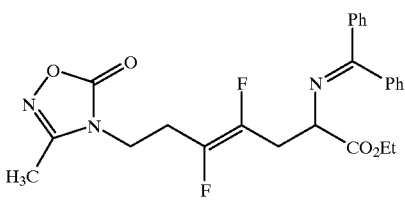

3h) The E isomer is isolated by chromatography from example 3g.

3) The product of step 3h is subjected to sonication in acetic acid/water in the presence of Zinc. This followed by aqueous acid hydrolysis to afford the title product.

EXAMPLE 4

(2R/S,4Z)-2-Amino-4,5-difluoro-6-(1-iminoethylamnino)-hept-4-enoic acid

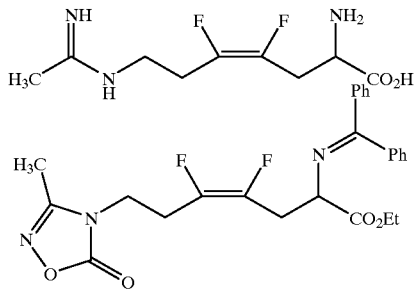

4a) The Z isomer is isolated by chromatography from example 3g.

4) The product of step 4a is subjected to sonication in acetic acid/water in the presence of Zinc. This is followed by aqueous acid hydrolysis to afford the title product.

EXAMPLE 5

(2S, 4Z)-2-Amino-4-Fluoro-6-(1-iminoethylamino)-hept-4-enoic acid

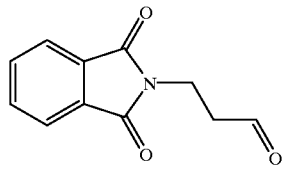

5a) Oxalyl chloride (110 ml, 220 mmol) was placed in a dry ice bath and cooled to −74° C. To the reaction mixture dimethyl sulfoxide (31.9 ml, 450 mmol) was added and stirred 30 minutes. To the reaction mixture N-(3-hydroxypropyl)phthalimide (40.5 g, 200 mmol) in dichloromethane (200 ml) was added and stirred 30 minutes. To the reaction mixture triethyl amine (125 ml, 900 mmol) was added and stirred 60 minutes. To the reaction mixture 350 ml of water was added. The layers were separated and the aqueous layer was washed with hexane. The organic layers were combined and washed with 5N HCl and saturated sodium hydrogen carbonate, dried over magnesium sulfate and concentrated to give 3.46 g of crude product. Mass Spectrometry indicated an M+H at 204.1, an M+NH$_4$ at 221.2.

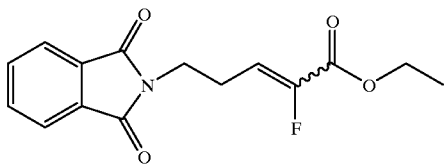

5b) Triethyl 2-fluoro-2-phosphonoacetate (3.62 ml, 17.9 mmol) in dichloromethane (50 ml) was placed in an ice bath and cooled to −1.8° C. To the reaction mixture 1,8-diazabicyclo [5,4,0]undec-7-ene (3.08 ml, 20.3 mmol) was added and stirred 30 minutes. To the reaction mixture, the product of step 5a (3.3 g, 16.2 mmol) was dissolved in dichloromethane (50 ml) and added to the reaction mixture and stirred 60 minutes. The reaction mixture was allowed to warm to room temperature. The reaction was quenched with 1 N Potassium hydrogen sulfate. The layer were separated. The organic layer was dried over Magnesium sulfate and concentrated under vacuum to give 3.57 g of a dark yellow oily product. Crude yield 75%. Mass Spectrometry indicated an M+H at 292, an M+NH$_4$ at 309.

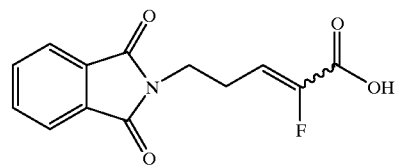

5c) The ester from step 5b (4.0 g, 13.7 mmol) was dissolved in a solution of acetone (160 ml), water (80 ml), and concentrated HCl (40 ml) and stirred overnight. The reaction mixture was refluxed for 24 hours. The reaction mixture was allowed to cool and the solvent was stripped. The residue was partitioned between sodium hydrogen carbonate and ethyl acetate. The organic layer was dried over magnesium sulfate and concentrated under vacuum to give 5.65 g of a orange crude product. Crude yield 100%. Mass Spectrometry indicated an M+H at 264.1, an M+NH$_4$ at 281.2.

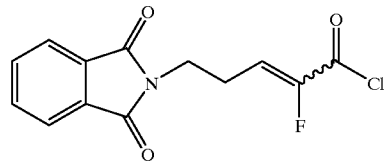

5d) The acid from step 5b (2.81 g, 10.7 mmol) was dissolved in dichloromethane (30 ml). To the reaction mixture oxalyl chloride (10.0 ml, 20.0 mmol) and dimethyl formamide (0.5 ml) were added. The reaction mixture was stirred 3 hours. The solvent was stripped. Mass Spectrometry indicated an M+H at 282.2, an M+NH$_4$ at 299.2.

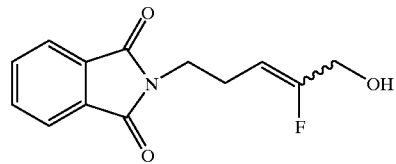

5e) The acid chloride from step 5c (2.81 g, 10.0 mmol) was dissolved in Dimethyl formamide (75 ml). To the reaction mixture Sodium borohydride (1.20 g, 31.7 mmol) was added and stirred 2 hours. To the reaction mixture Methanol (150 ml) and Acetic acid (150 ml) was added. The solvent was stripped. Mass Spectrometry indicated an M+H at 250.2.

5f) Chromatography resolution affords the separate E and Z isomers.

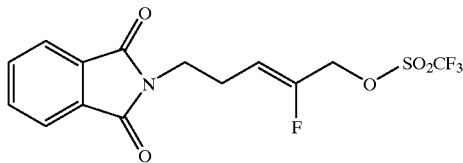

5g) The Z isomer from step 5e is allowed to react with triflic anhydride and pyridine in methylene chloride to afford the triflate.

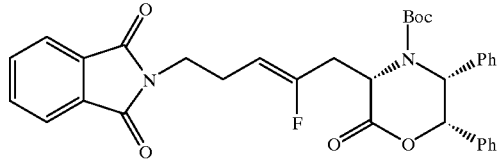

5h) The Williams' protected glycine (purchased from Aldrich) is allowed to react with LiHMDS in anhydrous THF at −78° C. This is followed by addition of the product of step 5f. Isolation and purification affords the title compound.

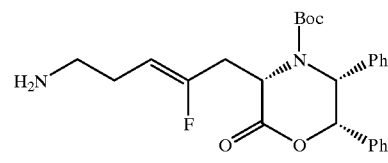

5i) The product of step 5g is allowed to react with hydrazine in ethanol followed by base to afford the title compound.

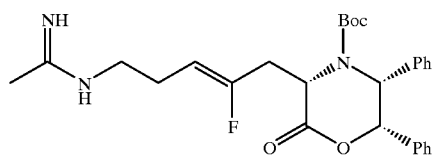

5j) The product oh step 5h is allowed to react with ethyl acetimidate in ethanol to afford the title compound.

5) The product of step 5i is allowed to stir in a mixture of liquid ammonia and sodium metal. Isolation and purification affords the title product.

EXAMPLE 6

(2S, 4E) 2-Amino-4-Fluoro-6-(1-iminoethylamino)-hept-4-enoic acid

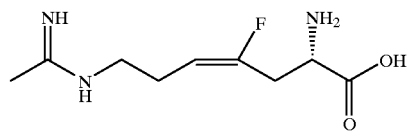

6a) Oxalyl chloride (110 ml, 220 mmol) was placed in a dry ice bath and cooled to −74° C. To the reaction mixture Dimethyl sulfoxide (31.9 ml, 450 mmol) was added and stirred 30 minutes. To the reaction mixture N-(3-hydroxypropyl)phthalimide (40.5 g, 200 mmol) in dichloromethane (200 ml) was added and stirred 30 minutes. To the reaction mixture triethyl amine (125 ml, 900 mmol) was added and stirred 60 minutes. To the reaction mixture 350 ml of water was added. The layers were separated and the aqueous layer was washed with hexane. The organic layers were combined and washed with 5N HCl and saturated Sodium hydrogen carbonate, dried over Magnesium sulfate and concentrated to give 3.46 g of crude product. Mass Spectrometry indicated an M+H at 204.1, an M+NH$_4$ at 221.2.

6b) Triethyl 2-fluoro-2-phosphonoacetate (3.62 ml, 17.9 mmol) in dichloromethane (50 ml) was placed in an ice bath and cooled to −1.8° C. To the reaction mixture 1,8-diazabicyclo[5,4,0]undec-7-ene (3.08 ml, 20.3 mmol) was added and stirred 30 minutes. To the reaction mixture, the product of step 6a (3.3 g, 16.2 mmol) is dissolved in dichloromethane (50 ml) and added to the reaction mixture and stirred 60 minutes. The reaction mixture was allowed to warm to room temperature. The reaction was quenched with 1 N Potassium hydrogen sulfate. The layers were separated. The organic layer was dried over Magnesium sulfate and concentrated under vacuum to give 3.57 g of a dark yellow oily product. Crude yield 75%. Mass Spectrometry indicated an M+H at 292, an M+NH$_4$ at 309.

6c) The ester from step 6b (4.0 g, 13.7 mmol) was dissolve in a solution of acetone (160 ml), water (80 ml), and concentrated HCl (40 ml) and stirred overnight. The reaction mixture was refluxed for 24 hours. The reaction mixture was allowed to cool and the solvent was stripped. The residue was partitioned between Sodium hydrogen carbonate and Ethyl acetate. The organic layer was dried over Magnesium sulfate and concentrated under vacuum to give 5.65 g of a orange crude product. Crude yield 100%. Mass Spectrometry indicated an M+H at 264.1, an M+NH$_4$ at 281.2.

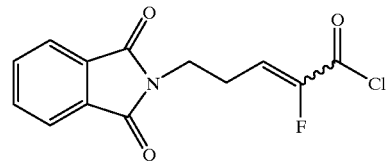

6c) The acid from step 6b (2.81 g, 10.7 mmol) was dissolved in dichloromethane (30 ml). To the reaction mixture Oxalyl chloride (10.0 ml, 20.0 mmol) and Dimethyl formamide (0.5 ml). The reaction mixture stirred 3 hours. The solvent was stripped. Mass Spectrometry indicated an M+H at 282.2, an M+NH$_4$ at 299.2.

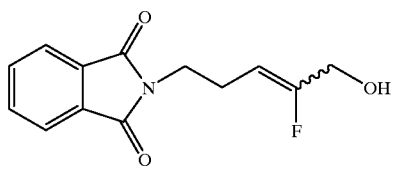

6d) The acid chloride from step 6c (2.81g, 10.0 mmol) was dissolved in Dimethyl formamide (75 ml). To the reaction mixture Sodium borohydride (1.20 g, 31.7 mmol) was added and stirred 2 hours. To the reaction mixture Methanol (150 ml) and Acetic acid (150 ml) was added. The solvent was stripped. Mass Spectrometry indicated an M+H at 250.2.

6e) Chromatography resolution affords the separate E and Z isomers.

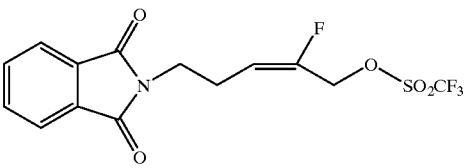

6f) The E isomer from step 6e is allowed to react with triflic anhydride and pyridine in methylene chloride to afford the triflate.

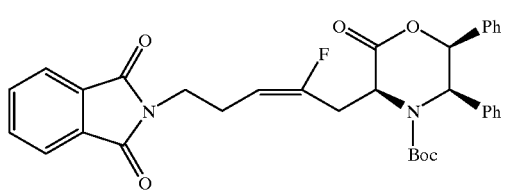

6g) The Williams' protected glycine (purchased from Aldrich) is allowed to react with LiHMDS in anhydrous THF at −78° C. This is followed by addition of the product of step 6f. Isolation and purification affords the title compound.

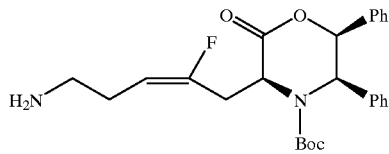

6h) The product of step 6g is allowed to react with hydrazine in ethanol followed by base to afford the title compound.

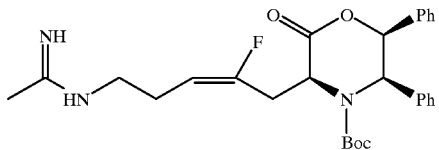

6i) The product oh step 6h is allowed to react with ethyl acetimidate in ethanol to afford the title compound.

6) The product of step 6i is allowed to stir in a mixture of liquid ammonia and sodium metal. Isolation and purification affords the title product.

The activity of the above listed compounds can be determined in the following assays:

Citrulline Assay for Nitric Oxide Synthase

Nitric oxide synthase (NOS) activity is measured by monitoring the conversion of [$^3$H]-arginine to [$^3$H]-citrulline (Bredt and Snyder, Proc. Natl. Acad. Sci. U.S.A., 87, 682–685, 1990 and Misko et al, Eur. J. Pharm., 233, 119–125, 1993). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a lambda cDNA library made from RNA extracted from a colon sample from a patient with ulcerative colitis. The cDNA for human endothelial constitutive NOS (hecNOS) is isolated from a lambda cDNA library made from RNA extracted from human umbilical vein endothelial cells (HUVEC) and the cDNA for human neuronal constitutive NOS (hncNOS) is isolated from a lambda cDNA library made from RNA extracted from human cerebellum obtained from a cadaver. The recombinant enzymes are expressed in Sf9 insect cells using a baculovirus vector (Rodi et al, in The Biology of Nitric Oxide Pt. 4: Enzymology, Biochemistry and Immunology; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 µL of enzyme is added to 40 µL of 50 mM Tris (pH 7.6) in the presence or absence of test compounds and the reaction initiated by the addition of 50 µL of a reaction mixture containing 50 mM Tris (pH 7.6), 2.0 mg/mL bovine serum albumin, 2.0 mM DTT, 4.0 mM CaCl$_2$, 20 µM FAD, 100 µM tetrahydrobiopterin, 0.4–2.0 mM NADPH and 60 µM L-arginine containing 0.9 µCi of L-[2,3-$^3$H]-arginine. The final concentration of L-arginine in the assay is 30 µM. For hecNOS or hncNOS, calmodulin is included at a final concentration of 40–100 nM. Following incubation at 37° C. for 15 minutes, the reaction is terminated by addition of 300 µL of cold stop buffer containing 10 mM EGTA, 100 mM HEPES, pH 5.5 and 1 mM citrulline. [$^3$H]-Citrulline is separated by chromatography on Dowex 50 W X-8 cation exchange resin and radioactivity determined with a liquid scintillation counter. Results are reported as the IC$_{50}$ values of compounds for hiNOS, hecNOS and hncNOS.

In vivo Assay

Rats are treated with an intraperitoneal injection of 10–12.5 mg/kg of endotoxin (LPS) to induce systemic expression of inducible nitric oxide synthase, resulting in markedly elevated plasma nitrite/nitrate levels. Compounds are administered orally 1 hour prior to LPS administration and plasma nitrite/nitrate levels are determined 5 hours following LPS administration.

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 mL of buffer containing L-arginine (30 mM) +/− inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, Analytical Biochemistry, 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 25–45 mg in weight and one or two explants per well are placed into 48 well culture plates with 500 µL of culture media per well. The culture media was a custom modification of Minimum Essential Medium(Eagle) with Earle's salts (GibcoBRL) prepared without L-Arginine, without L-Glutamine and without phenol red and supplemented before use with 100 µM L-Arginine (Sigma), 2 mM L-glutamine, 1× HL-1 supplement (BioWhittaker), 50 mg/ml ascorbic acid (Sigma) and 150 pg/ml recombinant human IL-1β (RD Systems) to induce nitric oxide synthase. Compounds are then added in 10 µL aliquots and the explants incubated at 37 degrees C. with 5% CO$_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, Anal. Biochem., 214, 11–16, 1993). All samples are done in quadruplicate. The explants are weighed and the nitrite levels normalized to weight. Unstimulated controls are cultured in media in the absence of recombinant human IL-1β. IC$_{50}$ values are determined from plotting the percent inhibition of nitrite production at six different concentrations of inhibitor.

What is claimed:
1. A compound of formula I

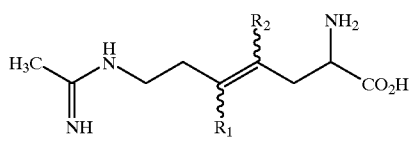

I or a pharmaceutically acceptable salt thereof, wherein:
$R_1$ is selected from the group consisting of H, halo and alkyl which may be optionally substituted by one or more halo;
$R_2$ is selected from the group consisting of H, halo and alkyl which may be optionally substituted by one or more halo;
with the proviso that at least one of $R_1$ or $R_2$ contains a halo.

2. The compound of claim 1 having a structure corresponding to Formula II:

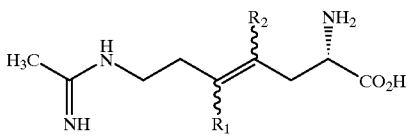

II or a pharmaceutically acceptable salt thereof, wherein:
$R_1$ is selected from the group consisting of H, halo and alkyl which may be optionally substituted by one or more halo;
$R_2$ is selected from the group consisting of H, halo and alkyl which may be optionally substituted by one or more halo;
with the proviso that at least one of $R_1$ or $R_2$ contains a halo.

3. The compound of claim 1 having a structure corresponding to Formula III:

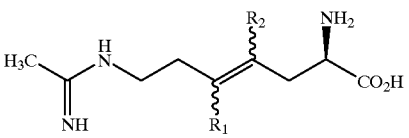

III or a pharmaceutically acceptable salt thereof, wherein:
$R_1$ is selected from the group consisting of H, halo and alkyl which may be optionally substituted by one or more halo;
$R_2$ is selected from the group consisting of H, halo and alkyl which may be optionally substituted by one or more halo;
with the proviso that at least one of $R_1$ or $R_2$ contains a halo.

4. The compound of claim 1 wherein:
$R_1$ is selected from the group consisting of H and $C_1$–$C_3$ alkyl which is optionally substituted by one or more halo, and
$R_2$ is fluorine.

5. The compound of claim 1 wherein:
$R_1$ is H; and
$R_2$ is fluorine.

6. The compound of claim 1 wherein:
$R_1$ is halo; and
$R_2$ is halo.

7. The compound of claim 1 wherein:
$R_1$ is fluorine; and
$R_2$ is fluorine.

8. The compound of claim 1 wherein the compound is the S enantiomer.

9. The compound of claim 1 wherein the compound is the R enantiomer.

10. The compound of claim 1 wherein the compound is the E isomer.

11. The compound of claim 1 wherein the compound is the Z isomer.

12. A compound selected from the group consisting of
(2S,4E/Z)-2-Amino-5-Fluoro-6-(1-iminoethylamino)-hept-4-enoic acid;
(2S,4E)-2-Amino-5-Fluoro-6-(1-iminoethylamino)-hept-4-enoic acid;
(2R,S,4E/Z)-2-Amino-4,5-difluoro-6-(1-iminoethylamino)-hept-4-enoic acid;
(2R/S,4Z)-2-Amino-4-Fluoro-6-(1-iminoethylamino)-hept-4-enoic acid;
(2S,4Z)-2-Amino-4-Fluoro-6-(1-iminoethylamino)-hept-4-enoic acid; and
(2S,4E)-2-Amino-4-Fluoro-6-(1-iminoethylamino)-hept-4-enoic acid.

13. A pharmaceutical composition comprising a compound of claim 1.

14. A method of inhibiting nitric oxide synthesis in a subject in need of such inhibition by administering a therapeutically effective amount of a compound of claim 1.

15. A method of selectively inhibiting nitric oxide produced by inducible nitric oxide synthase over nitric oxide produced by the constitutive forms of nitric oxide synthase in a subject in need of such inhibition by administering a therapeutically an effective amount of a compound of claim 1.

16. A method of lowering nitric oxide levels in a subject in need of such by administering a therapeutically effective amount of a compound of claim 1.

17. A method of lowering nitric oxide levels in a subject in need of such by administering a therapeutically effective amount of a pharmaceutical composition comprising a compound of claim 1.

18. The method of claim 17 wherein said pharmaceutical composition comprises a combination of a selective COX-2 inhibitor and a compound of claim 1.

19. The compound of claim 1 wherein the compound is in the form of a pharmaceutically-acceptable salt.

20. The pharmaceutically-acceptable salt of claim 19 having at least one anionic counterion.

21. The pharmaceutically-acceptable salt of claim 20 wherein the anionic counterion is selected from the group consisting of a halide, a carboxylate, a sulfonate, a sulfate, a phosphate, a phosphonate, a resin-bound anion, and a nitrate.

22. The pharmaceutically-acceptable salt of claim 21 wherein the anionic counterion is a halide.

23. The pharmaceutically-acceptable salt of claim 22 wherein the halide is chloride.

24. The pharmaceutically-acceptable salt of claim 21 wherein the anionic counterion is a carboxylate.

25. The pharmaceutically-acceptable salt of claim 24 wherein the carboxylate is selected from the group consisting of formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (±)-mandelate, (R)-(−)-mandelate, (S)-(+)-mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)-lactate, D-(−)-lactate, pamoate, D-alpha-galacturonate, glycerate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, and L-pyroglutamate.

26. The pharmaceutically-acceptable salt of claim 21 wherein the anionic counterion is a sulfonate.

27. The pharmaceutically-acceptable salt of claim 26 wherein the sulfonate is selected from the group consisting of methanesulfonate, toluenesulfonate, benzenesulfonate, trifluoromethylsulfonate, ethanesulfonate, (±)-camphorsulfonate, naphthalenesulfonate, 1R-(−)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(N-morpholino)propane sulfonate, biphenylsulfonate, isethionate, and 1-hydroxy-2-naphthalenesulfonate.

28. The pharmaceutically-acceptable salt of claim 21 wherein the anionic counterion is a sulfate.

29. The pharmaceutically-acceptable salt of claim 28 wherein the sulfate is selected from the group consisting of sulfate, monopotassium sulfate, monosodium sulfate, and hydrogen sulfate.

30. The pharmaceutically-acceptable salt of claim 21 wherein the anionic counterion is a phosphate.

31. The pharmaceutically-acceptable salt of claim 30 wherein the phosphate is selected from the group consisting of phosphate, dihydrogen phosphate, potassium hydrogen phosphate, dipotassium phosphate, potassium phosphate, sodium hydrogen phosphate, disodium phosphate, sodium phosphate, calcium phosphate, and hexafluorophosphate.

32. The pharmaceutically-acceptable salt of claim 21 wherein the anionic counterion is a phosphonate.

33. The pharmaceutically-acceptable salt of claim 32 wherein the phosphonate is selected from the group consisting of vinylphosphonate, 2-carboxyethylphosphonate and phenylphosphonate.

34. The pharmaceutically-acceptable salt of claim 21 wherein the anionic counterion is a resin-bound anion.

35. The pharmaceutically-acceptable salt of claim 34 wherein the resin-bound anion is selected from the group consisting of a resin comprising polyacrylate and a resin comprising sulfonated poly(styrene divinylbenzene).

36. The pharmaceutically-acceptable salt of claim 21 wherein the anionic counterion is nitrate.

37. The pharmaceutically-acceptable salt of claim 20 wherein the anion is selected from the group consisting of DL-ascorbate, D-ascorbate, and L-ascorbate.

38. The pharmaceutically-acceptable salt of claim 19 having at least one cationic counterion.

39. The pharmaceutically-acceptable salt of claim 38 wherein the cationic counterion is selected from the group consisting of an ammonium cation, a alkali metal cation, an alkaline earth metal cation, a transition metal cation, and a resin-bound cation.

40. The pharmaceutically-acceptable salt of claim 39 wherein the cationic counterion is an ammonium cation.

41. The pharmaceutically-acceptable salt of claim 40 wherein the ammonium cation is selected from the group consisting of ammonium, methyl ammonium, dimethylammonium, trimethylammonium, tetramethylammonium, ethanolammonium, dicyclohexylammonium, guanidinium, and ethylenediammonium cation.

42. The pharmaceutically-acceptable salt of claim 39 wherein the cationic counterion is an alkali metal cation.

43. The pharmaceutically-acceptable salt of claim 42 wherein the alkali metal cation is selected from the group consisting of lithium cation, sodium cation, potassium cation, and cesium cation.

44. The pharmaceutically-acceptable salt of claim 39 wherein the cationic counterion is an alkaline earth metal cation.

45. The pharmaceutically-acceptable salt of claim 44 wherein the alkaline earth metal cation is selected from the group consisting of beryllium cation, magnesium cation, and calcium cation.

46. The pharmaceutically-acceptable salt of claim 39 wherein the cationic counterion is a transition metal cation.

47. The pharmaceutically-acceptable salt of claim 46 wherein the transition metal cation is a zinc cation.

48. The pharmaceutically-acceptable salt of claim 39 wherein the cationic counterion is a resin-bound cation.

49. The pharmaceutically-acceptable salt of claim 48 wherein the resin-bound cation is a cationically functionalized poly(styrene divinylbenzene) resin.

50. The pharmaceutically-acceptable salt of claim 49 wherein the resin-bound cation is an aminated poly(styrene divinylbenzene) resin.

51. The pharmaceutically-acceptable salt of claim 48 wherein the resin-bound cation is a cationically functionalized polyacrylic resin.

52. The pharmaceutically-acceptable salt of claim 48 wherein the resin-bound cation is an aminated polyacrylic resin.

53. A method of treating or preventing an inflammation related condition in a subject in need of such treatment or prevention comprising:
administering a treatment or prevention effective amount of a compound of formula I

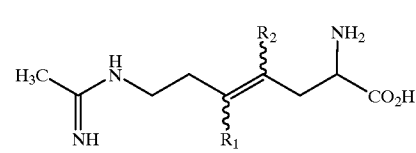

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R_1$ or $R_2$ contains a halo to a subject in need of such treatment or prevention.

54. The method of claim 53 wherein said inflammation related condition is an arthritis condition.

55. The method of claim 54 wherein said arthritis condition is osteoarthritis.

56. The method of claim 54 wherein said arthritis condition is rhumatoid arthritis.

57. The method of claim 53 wherein said inflammation related condition is post-operative inflammation.

58. The method of claim 57 wherein said post-operative inflammation is associated with ophthalmic surgery.

59. The method of claim 58 wherein said ophthalmic surgery is cataract surgery.

60. The method of claim 53 wherein said inflammation related condition is associated with an infection.

61. The method of 60 wherein said infection is sepsis.

62. The method of claim 61 wherein said infection is caused by a virus.

63. The method of claim 53 wherein said inflammation related condition is inflammatory bowel syndrome.

64. The method of claim 53 wherein said inflammatory related condition is caused by injury.

65. The method of claim 53 wherein said inflammatory related condition is pulmonary inflammation.

66. The method of claim 65 wherein said pulmonary inflammation is caused by cystic fibrosis.

67. A method of treating or preventing a malignant neoplasia in a subject in need of such treatment or prevention comprising:
   administering a treatment or prevention effective amount of a compound of formula I

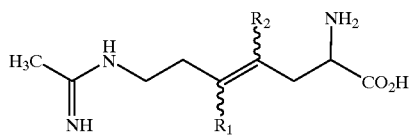

or a pharmaceutically acceptable salt thereof, wherein:
   $R^1$ is selected from the group consisting of H, halo and alkyl which is optionally substituted by one or more halo;
   $R^2$ is selected from the group consisting of H, halo and alkyl which is optionally substituted by one or more halo;
   with the proviso that at least one of $R_1$ or $R_2$ contains a halo to a subject in need of such treatment or prevention.

68. The method of claim 67 wherein said cancer is an epithelial cell-derived neoplasia.

69. The method of claim 68 wherein said epithelial cell-derived neoplasia is a gastrointestinal cancer.

70. The method of claim 69 wherein said epithelial cell-derived neoplasia is colon cancer.

71. The method of claim 69 wherein said epithelial cell derived neoplasia is lung cancer.

72. The method of claim 68 wherein said epithelial cell derived neoplasia is prostate cancer.

73. The method of claim 68 wherein said epithelial cell derived neoplasia is cervical cancer.

74. The method of claim 68 wherein said epithelial cell derived neoplasia is breast cancer.

75. The method of claim 67 wherein said malignant neoplasia is mesenchymal tissue derived.

76. A method of treating addiction in a subject in need of such treatment comprising:
   administering a treatment effective amount of a compound of formula I

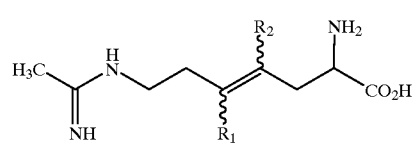

or a pharmaceutically acceptable salt thereof, wherein:
   $R^1$ is selected from the group consisting of H, halo and alkyl which is optionally substituted by one or more halo;
   $R^2$ is selected from the group consisting of H, halo and alkyl which is optionally substituted by one or more halo;
   with the proviso that at least one of $R_1$ or $R_2$ contains a halo; to a subject in need of such treatment.

* * * * *